United States Patent [19]

Dunn et al.

[11] Patent Number: 4,932,972

[45] Date of Patent: * Jun. 12, 1990

[54] PROSTHETIC LIGAMENT

[75] Inventors: Richard L. Dunn, Birmingham; Danny H. Lewis, Hartselle, both of Ala.; Thomas W. Sander, Memphis, Tenn.; James A. Davidson, Germantown, Tenn.; Neil B. Beals, Memphis, Tenn.; Yancy L. Gill, Smyrna, Ga.

[73] Assignee: Richards Medical Company, Memphis, Tenn.

[*] Notice: The portion of the term of this patent subsequent to Dec. 13, 2005 has been disclaimed.

[21] Appl. No.: 186,330

[22] Filed: Apr. 26, 1988

Related U.S. Application Data

[60] Division of Ser. No. 64,634, Jun. 22, 1987, Pat. No. 4,740,850, which is a continuation-in-part of Ser. No. 840,298, Mar. 14, 1986, Pat. No. 4,731,084.

[51] Int. Cl.$^5$ .............................................. A61F 2/08
[52] U.S. Cl. ........................................ 623/13; 623/16
[58] Field of Search ............................ 623/13, 1, 66; 128/335.5

[56] References Cited

U.S. PATENT DOCUMENTS

| | | |
|---|---|---|
| 3,953,896 | 5/1976 | Treace . |
| 4,149,277 | 4/1979 | Bokros ................... 623/13 |
| 4,187,558 | 2/1980 | Dahlen et al. . |
| 4,301,551 | 11/1981 | Dore et al. ............... 623/13 |
| 4,413,110 | 11/1983 | Kavesh et al. . |
| 4,503,568 | 3/1985 | Madras .................... 623/1 |
| 4,550,730 | 11/1985 | Shalaby et al. ........... 128/335.5 |
| 4,584,722 | 4/1986 | Levy et al. ............... 623/13 |
| 4,587,163 | 5/1986 | Zachariades .............. 623/13 X |
| 4,610,688 | 9/1986 | Silvestrini et al. ........ 623/2 X |
| 4,662,886 | 5/1987 | Moorse et al. ............ 623/13 |
| 4,712,542 | 12/1987 | Daniel et al. ............ 128/92 VK X |

FOREIGN PATENT DOCUMENTS

2159846 12/1985 United Kingdom .................. 623/13

OTHER PUBLICATIONS

"New Technology, New Horizons," Allied Corporation, 1985 Brochure for Spectra-900 ®.
C. Frank et al., "Normal Ligament Properties and Ligament Healing" 196. Clinical Orthopaedics and Related Research, Synthetic Ligaments and Tendons, (H. Alexander & A. Weiss eds. Jun. 1985) at 15.
D. Butler et al., "On the Interpretation of Our Anterior Cruciat Ligament Data", Clinical Orthopaedics, supra at 26.

(List continued on next page.)

Primary Examiner—Alan W. Cannon
Attorney, Agent, or Firm—Kirkpatrick & Lockhart

[57] ABSTRACT

A prosthetic ligament assembly includes a nonaugmented prosthetic ligament for permanently replacing a natural ligament spanning first and second body members, such as the femur and tibia, and a bone screw adapted for tensioning the prosthetic ligament during implantation. The prosthetic ligament includes a load bearing member intertwined into a plain braid from a plurality of biocompatible, high strength, ultra high molecular weight polyethylene yarns. Each yarn includes at least fifty fibers and has a tensile strength greater than or equal to about 100,000 psi. The load bearing member has a gage section and a loop at each end thereof for anchoring the load bearing member to the body members. The load bearing member is preloaded to remove slack therefrom. The load bearing member may be used alone or may be formed into a hollow braid having a core disposed within the hollow portion of the braid to permit radiographic visualization of the prosthetic ligament. A sheath may be friction fit or molded onto the exterior of the gage section. The assembly also includes one or two bone screws for complimentary engagement with the loops of the load bearing member. The bone screws have a tapered section extending beneath the head of the screw to the shank for tensioning the prosthetic ligament during implantation.

7 Claims, 3 Drawing Sheets

OTHER PUBLICATIONS

G. Strum & Larson, "Clinical Experience and Early Results of Carbon Fiber Augmentation of Anterior Cruciate Reconstruction of the Knee," Clinical Orthopaedics, supra at 26.

Prosthetic Ligament Reconstruciton of the Knee, 2d Annual Symposium Department of Continuing Education in the Health Sciences, UCLA Extension, and the school of Medicine, UCLA (Mar. 21-24, 1985).

C. Peterson et al., "A segmented Polyurethane Composite Prosthetic Anterior Cruciate Ligament In Vivo Study" 19 Journal of Biomedical Materials Research 589 (1985).

A. Ellison, "Studies on the Prosthetic Replacement of the Anterior Cruciate Ligament", Thesis to American Orthopaedic Association, Jan. 1, 1976, Relevant Pages Enclosed.

G. K. McPherson et al., "Experimental Mechanical and Histologic Evaluation of the Kennedy Ligament Augmentation Device", Clinical Orthopaedics, supra at 186.

C. Bolton & W. Bruchman, "The GORE-TEX TM Expanded Polytetrafluoroethylene Prosthetic Ligament, An In Vitro and In Vito Evaluation", Clinical Orthopaedics, supra as 202.

PROSTHETIC LIGAMENT

This is a divisional of copending application Ser. No. 064,634 filed on June 22, 1987 now U.S. Pat. No. 4,790,850 which is a continuation-in-part of application Ser. No. 840,298 filed or Mar. 14, 1986 now U.S. Pat. No. 4,731,084.

BACKGROUND OF THE INVENTION

1. Field of the Invention

The present invention relates generally to prosthetic devices and more particularly to a permanent prosthethic ligament.

2. Description of the Prior Art

Recently, interest has increased in the development of prosthetic ligaments and tendons. One difficulty encountered in designing such prostheses arises from the strength and flexibility requirements for such devices. Due to the flexible nature of ligaments and tendons, prosthetic devices designed to replace natural ligaments and tendons tend to undergo plastic and constructional deformation, possibly resulting in a change in stiffness characteristics over time.

The goal of ligament replacement is to permit the recipient to return to his or her full range of activity as soon as possible. To that end, researchers have attempted by several means to mimic some of the parameters of strength, flexibility, extension and/or recovery found in natural ligaments. Natural ligaments are bands of flexible fibrous connective tissue which join bones or hold organs in place. The mechanical properties of a natural ligament were reported by D. Butler et al., "On the Interpretation of Our Anterior Cruciate Ligament Data", 196 CLINICAL ORTHOPAEDICS AND RELATED RESEARCH, SYNTHETIC LIGAMENTS AND TENDONS (H. Alexander & A. Weiss eds. June 1985), at 26. Butler et al. measured the stiffness of the anterior cruciate ligament-bone unit. The stiffness measured for young donors was $182\pm56$ kilonewtons per meter ($1038\pm0.32$ lb/in) and for older donors was $129\pm39$ kilonewtons per meter ($735.3\pm0.16$ lb/in).

The length of the adult anterior cruciate ligament (ACL) ranges between 27 to 39 mm (1.06–1.56 inches). The stiffness of the human ACL is reported to decrease roughly 30% with increasing age. Peak loads experienced by the ACL can range between 170 N (about 38 lbs.) for normal walking to 700 N (about 158 lbs.) for occasional jolts, such as tripping or jumping to one side. Under extreme loads, ranging between 501 to 1730 N (113–389 lbs.), the human ACL can tear. The maximum force tolerated for tissue obtained from young donors was $1730\pm66$ N (about $389\pm15$ lbs.). Extreme loads placed on prosthetic ligaments cause them to experience plastic deformation, an irreversible change in the microstructure of the device, a phenomenon often referred to as "creep". Prosthetic ligaments which have undergone creep are more susceptible to damage.

Laxity in the human ACL is measured clinically by means of the anterior drawer test (90° flexion) or the Lachman test (20% flexion). It is reported that a knee exhibiting an anterior drawer greater than 10–15 mm (0.39–0.59 inch) under a load of 89 N (20 lbs.) requires repair. It is also reported that stable knees generally have an anterior drawer of less than 6–8 mm (0.23–0.31 inch); and that laxity relative to a patient's other healthy knee of greater than 2 mm (0.08 inch) indicates poor ACL support in the injured knee.

Often, torn or ruptured human ACL's are repaired with sutures, or augmented with autogenous tissue such as the patellar tendon. This type of repair requires many weeks of recovery. A prosthetic device should eliminate long term recovery and restore stability to the involved joint. However, it is important that creep and changes in stiffness of the prosthesis be minimized so that laxity does not return to the involved joint over time. A stiffness similar to that of the natural ligament is desirable.

Attempts to repair or replace damaged ligaments have been varied and generally inadequate for immediately restoring full strength and stability to the involved joint. Workers in the field have transferred natural tissue from other parts of a patient's body to the involved joint. Synthetic materials have also been used to augment natural tissue transfers. A number of techniques employing carbon fiber-type or polypropylene augmentation devices are described in CLINICAL ORTHOPAEDICS, supra. For example, a flat strap-like braid of polypropylene fibers was used to augment natural tissue grafts in studies conducted on goats. See G. McPherson et al., "Experimental Mechanical and Histologic Evaluation of the Kennedy Ligament Augmentation Device", CLINICAL ORTHOPAEDICS, supra at 186. The time required for the recipient to return to normal activity is generally about one year or longer.

As an alternative to natural tissue grafts, xenografts, tissue grafts from a species other than the recipient species, have been implanted to replace natural ligaments. Like the natural tissue grafts and the augmentation devices, xenografts have tended to be unpredictable in the long term for restoring full strength and stability to the involved joint.

Another type of prosthetic ligament relies on bone ingrowth to aid in the attachment of the ligament to bone. Bone ingrowth strengthens the attachment but requires about six months to complete. In the meantime, the recipient's mobility should be restricted. Dahlen et al. U.S. Pat. No. 4,187,558, which issued on Feb. 12, 1980, describes a flexible braid made of Dacron (polyethylene terephthalate), encased in silicone rubber. A velour covered collar at one or both ends of the braid aids in attachment to the bone and promotes bone ingrowth to anchor the device.

Several permanent, nonaugmented prosthetic ligaments have been developed. A permanent prosthesis is one which assumes its full strength initially upon implantation, is not intended to gradually resorb or disintegrate over time and does not depend on autographs or "regrown" natural ligament tissue for its ultimate success. Dore et al. U.S. Pat. No. 4,301,551, which issued on Nov. 24, 1981 describes a deformable silicone core surrounded by a tensionable wrapping of polymeric or stainless steel threads wound in a helical angle about the core. The core is the load bearing member and is capable of large elastic deformation in response to compression by the threads when the device is stretched. Two rigid plastic or stainless steel rods, one at each end of the core, connect the device to the bones of a joint.

Treace U.S. Pat. No. 3,953,896, which issued on May 4, 1976 describes a prosthetic ligament made of a flexible, ultra high molecular weight polyethylene rod. Stainless steel sleeves and polyethylene nuts on each end of the flexible rod hold the prosthetic ligament to the bones.

A third permanent, nonaugmented prosthetic ligament reported by C. Bolton and W. Bruchman, "The GORE-TEX TM Expanded Polytetrafluoroethylene Prosthetic Ligament", CLINICAL ORTHOPAEDICS, supra at 202, is constructed of bundles of Gore-Tex ® fibers arranged in a braided configuration. The braid is fixed by bone screws placed through eyelets at each end of the braid. According to a description of the Gore-Tex ® ligament in a product brochure published by the manufacturer, the ultimate tensile strength of the device is approximately 1160 lbs. The product brochure indicates that prior to packaging, each Gore-Tex ® ligament is tested to 1000 lbs. as a quality control measure.

Testing of a prosthesis composed of a continuous weave of Dacron fibers in the form of a braid with a hollow central core gave poor results. The investigators concluded, as reported in A. Ellison, "Studies on the Prosthetic Replacement of the Anterior Cruciate Ligament" (thesis to American Orthopaedic Association, Jan. 1, 1976), that Dacron will never be satisfactory for an anterior cruciate ligament prosthesis.

Zachariades U.S. Pat. No. 4,587,163 discloses an isotropic semicrystalline morphology of ultra high molecular weight polyethylene for use in making artificial tendons or ligament protheses. The artificial tendon can be sutured to a natural tendon segment. The polyethylene described by Zachariades is an ultradrawn melt crystallized ribbon-like structure.

A variety of means are disclosed to attach prosthetic ligaments to the appropriate body member. Bokros U.S. Pat. No. 4,149,277 discloses a ligament or tendon prosthesis which includes a loop at the bone joining end of a braided strand. The Dore patent referenced above employs rigid plastic or stainless steel rods and the Treace patent employs stainless steel sleeves and polyethylene nuts. The Gore-Tex ® ligament includes eyelets at each end to connect the ligament to bone.

As mentioned above, one problem often experienced by recipients of prosthetic ligaments is that the braided ligaments undergo constructional deformation after implant and, as a result, becomes too lax over time or after the first load is placed on the joint. Constructional deformation occurs when the fibers of the braided ligament prosthesis compact and undergo helical changes. There is a certain amount of "slack" in the prosthetic ligaments heretofore available which permits them to undergo constructional deformation with use. The prosthetic ligament lengthens and loses its tensioning capacity for the involved joint.

An object of the present invention is to provide a permanent nonaugmented prosthetic ligament having parameters of strength and flexibility that at least approximate those of a natural ligament. A further object of the present invention is to provide such a prosthetic ligament that does not depend solely upon bone ingrowth for strengthening the attachment to the bones of the involved joint, and thus, does not require long periods of recuperation before the recipient can resume a full range of normal activity. It is a further object of the present invention to provide a permanent ligament prosthesis which will minimize any observed increase in laxity with time and will undergo minimal constructional deformation after the first shock load.

SUMMARY OF THE INVENTION

The present invention provides a prosthetic ligament assembly and a prosthetic ligament for permanently connecting first and second body members, such as the femur and tibia. The prosthesis of the present invention is a permanent synthetic replacement for a natural ligament and does not depend solely upon the ingrowth of natural tissue to augment the connection between the two body members. Thus, it is believed that the recipient of the prosthetic ligament can return to a normal range of activity much more quickly than the recipient of a prosthetic ligament requiring augmentation with natural tissue. Furthermore, the strength provided by the prosthetic ligament of the present invention at least approximates the strength of a natural ligament to such an extent that recipients may resume normal activities.

The prosthetic ligament assembly includes a prosthetic ligament and one or more bone screws for complimentary engagement with the ligament.

The prosthetic ligament includes a nonaugmented load bearing member having a gage section for permanently spanning the distance between the first and second body members. The load bearing member is formed from a plurality of biocompatible, high strength polyethylene yarns. The yarns are intertwined into a braid. Each of the yarns includes at least fifty fibers and has a tensile strength greater than or equal to about 689 MPa (100,000 psi). Each fiber has an average diameter of less than 100 microns.

The load bearing member includes a looped extension on at least one end thereof continuous therewith for anchoring the prosthetic ligament to the first and/or second body members. The looped extension is preferably collapsible to a diameter approximately equal to the diameter of the gage section of the load bearing member.

The load bearing member is preferably preloaded to a degree which exceeds the maximum physiological load to which the prosthetic ligament will be exposed in vivo during normal activities and which is sufficient for removing slack from the load bearing member to avoid constructional deformation of the load bearing member without inducing plastic deformation of the fibers.

The gage section of the load bearing member may define a longitudinal bore therethrough. Means may be optionally disposed within the bore to permit radiographic visualization of the ligament after implantation. The visualization permitting means is preferably made of a biocompatible radiopaque material, such as a high strength block copolymer containing silicone oil, and has a diameter less than or equal to the diameter of the bore.

The prosthetic ligament may further include a sheath encasing the gage section of the load bearing member for preventing damage to the fibers. The sheath may be a tube friction fit onto the gage section or may be molded or otherwise put onto the gage section.

The bone screw of the prosthetic ligament assembly has a head portion, a shank and a tapered section extending beneath the head portion to the shank for tensioning the prosthetic ligament during implantation.

BRIEF DESCRIPTION OF THE DRAWINGS

The present invention can better be understood by reference to the drawings in which.

DETAILED DESCRIPTION OF THE PREFERRED EMBODIMENT

Figure 6:
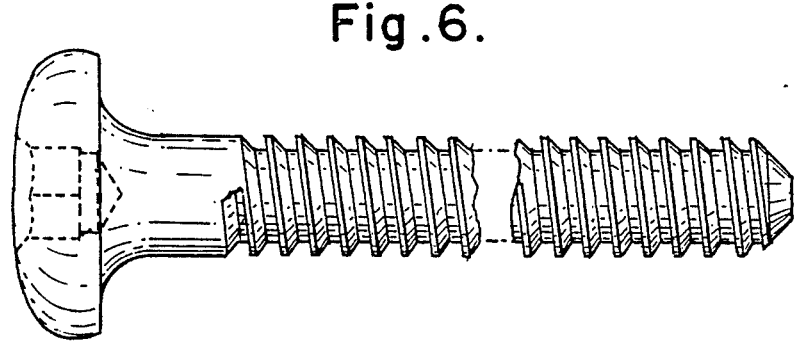
FIG. 6 is a view of the bone screw of the prosthetic ligament assembly of the present invention.

FIGS. 1 through 5 illustrate the preferred embodiments of the prosthetic ligament 10 of the present invention. FIG. 6 illustrates the bone screw 52, which together with prosthetic ligament 10 comprises the prosthetic ligament assembly of the present invention. Although the prosthetic ligament 10 is shown as connecting the femur and tibia, it should be recognized that the prosthetic ligament 10 can be used to connect other skeletal members and, depending upon the means of attachment employed, to support soft tissue organs in place. For purposes of describing the preferred embodiment of the prosthetic ligament and the prosthetic ligament assembly, however, the prosthetic ligament 10 is employed to permanently replace the natural anterior cruciate ligament of the human knee.

The prosthetic ligament 10 includes primarily a major load bearing member which has a gage section 20 and at least one looped extension 50 at one end thereof. A core 30 and sheath 40 may optionally be included. The load bearing member is formed from a plurality of high strength, biocompatible polyethylene yarns. There are at least fifty (50) fibers in each yarn. Each polyethylene fiber has an average diameter of less than about 100 microns (0.002 inch). Fiber tensile strength is greater than 689 MPa (100,000 psi). The yarns are parallel wound and the resulting bundles are intertwined to form a braid. A plurality of such high strength yarns, braided at the appropriate picks per inch, as hereinafter defined, provides a high strength load bearing member. Numerous fibers add to the life of the prosthetic ligament 10 because there are numerous surfaces to tolerate stress and abrasion.

Figure 2:
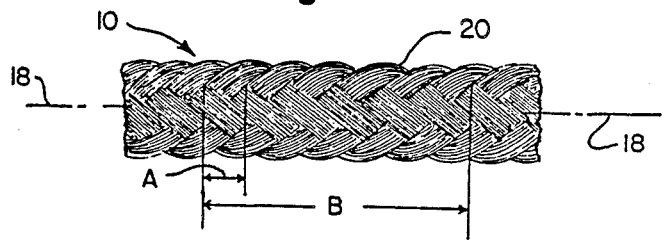
FIG. 2 is a view of the load bearing member of the present invention formed into a twill braid.
Figure 2A:
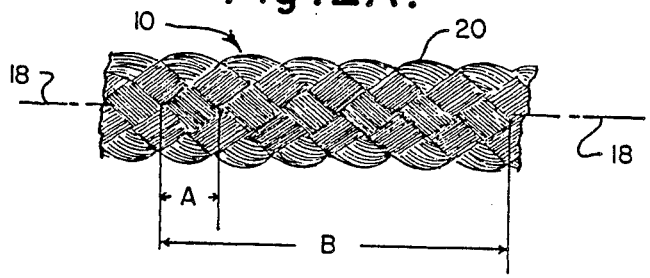
FIG. 2A is a view of the load bearing member of the present invention formed into a plain braid.
Figure 3:
FIG. 3 is a view of the load bearing member of FIG. 2 with an inner core.
Figure 4:
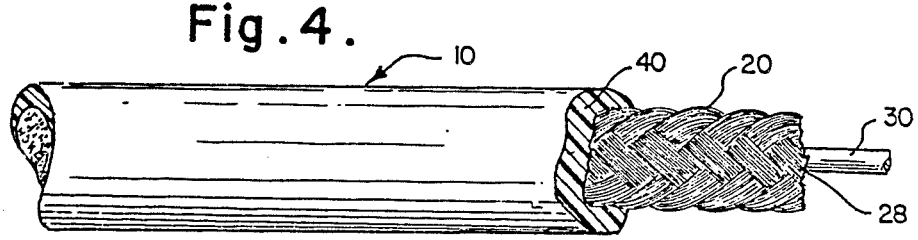
FIG. 4 is a view of the load bearing member of FIG. 2 with an inner core and an outer sheath.
Figure 5:
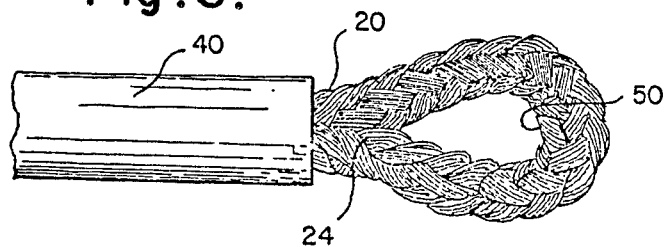
FIG. 5 is a view of one end of the load bearing member of FIG. 2 with a looped extension for anchoring the prosthetic ligament to the recipient.

In rope technology, the plain braid type, as shown in FIG. 2A, is defined in terms of picks/inch. For purposes of this specification, "pick" shall mean the crossing of one yarn bundle over another created by the braiding technique. Picks are counted along the longitudinal axis of the ligament. The greater the number of picks/inch, the tighter the braid. The preferred average diameter of the gage section 20 is about 4-6 mm (about 0.16-0.24 inches). A braid of 5-7 picks/inch provides the desired diameter. The section designated as "A" in FIG. 2A represents one pick. The section designated as B represents six picks. The braid shown in FIG. 2 is a twill braid. Comparable sections A, designating one pick and B designating six picks are shown. The best mode of the load bearing member developed to date is formed from a plain braid.

For purposes of the present invention, the term "fiber" shall mean the smallest unit and is synonymous with a single filament. The term "yarn" shall mean a plurality of fibers in a form suitable for weaving, braiding or otherwise intertwining to form, in the case of the subject invention, a prosthetic ligament.

The fibers form a porous surface. It is reported that pore sizes from about 0 to 100 microns enhance fibrous ingrowth and that pore sizes greater than 100 microns enhance bony ingrowth. Fibrous or bony ingrowth will not occur, however, in those places where sheath 40, which will be described in more detail below, covers the load bearing member.

The fibers must be made of a high strength, biocompatible organic polymer, preferably an ultra high molecular weight polyethylene. Kavesh et al. U.S. Pat. No. 4,413,110, which is hereby incorporated herein by reference, describes one process for the production of ultra high molecular weight polyethylene fibers which have a high tenacity and a high tensile modulus. Any suitable means for providing ultra high molecular weight polyethylene will suffice. The commercial embodiments of the polyethylene fibers described in the Kavesh patent, sold under the trademarks SPECTRA-900 TM and SPECTRA-1000 TM by Allied-Signal Inc., have a tensile strength of about 375,000–425,000 psi. The density of each SPECTRA TM fiber is between 0.5-1.5 g/cc.

As mentioned previously, ultra high molecular weight polyethylene for use in prosthetic ligaments is disclosed in Zachariades U.S. Pat. No. 4,587,163. However, the Zachariades material is not a multifilament like that used in the ligament 10 of the present invention. The ribbon like structure of the Zachariades material will not permit tissue ingrowth. More importantly, however, the Zachariades material is sintered and then drawn to produce a single filament with a strength to weight ratio much less than that of the fibers used to make the yarns of ligament 10 (40 MPa versus 2930 MPa).

The best mode developed to date of ligament 10 uses commercially available ultra high molecular weight polyethylene fibers, e.g. SPECTRA-900 TM or SPECTRA-1000 TM The preferred embodiment of ligament 10 can be described as having one hundred twenty (120) fibers in each yarn, formed into an 8-strand, 6-parallel wound plain braid ranging from 5-7 picks/inch to provide an average gage section diameter of about 4-6 mm. The SPECTRA-1000 TM fibers have a tenacity of 35 grams/denier with a specific gravity of about 0.97 and an average diameter of about 27 microns (0.0011 inch).

Prosthetic ligament 10 includes means, such as the looped extensions 50 of gage section 20 of the load bearing member, for anchoring the ligament 10 to the skeletal members 12, 14. One braided loop 50 is connected in a continuous braid to at least one end 24 or 26 of gage section 20. In the preferred embodiment, both ends 24 and 26 have loops 50. At least one, and preferably both, loops 50 are collapsible to a diameter approximately equal to the diameter of the gage section 20 to permit the ligament 10 to pass through the bone tunnel when the implant technique employing bone tunnels is used. The loops 50 are deformable to permit other types of fixation. The loops 50 are preferably formed by using a modified Eye-splice, but any suitable known splicing technique for forming continuous looped ends on a braided structure will suffice.

Figure 1:
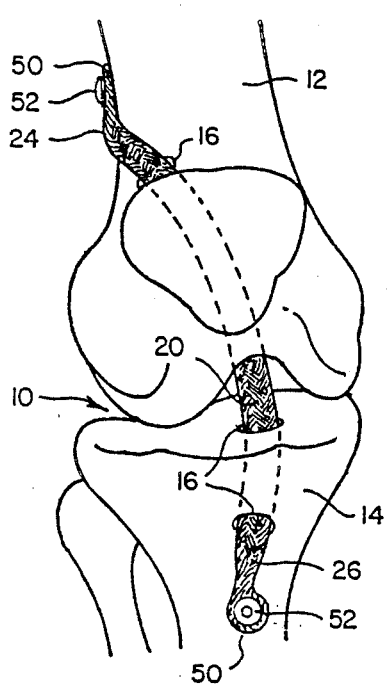
FIG. 1 is a view of the preferred embodiment of the prosthetic ligament assembly of the present invention joining the femur and tibia of a recipient by one of several known implant techniques.

The prosthetic ligament 10 can be placed in the recipient by any suitable surgical technique. FIG. 1 illustrates an example of the technique employing bone tunnels 16.

Ligament 10 may optionally include a sheath 40. The sheath 40 may be a tube having an internal diameter equal to or less than the diameter of the gage section 20 which is friction fit onto the gage section 20. The sheath 40 must be thick enough to withstand the abrasion to which it may be subjected. In one embodiment for use in replacing a cruciate ligament, the sheath 40 is about 1/16 inch thick. The thickness may vary depending upon the desired use of the prosthetic ligament 10.

The sheath 40 may also be formed onto the gage section 20. Care should be taken, however, to avoid over-heating the load bearing member. Excessive heat can damage the fibers. Regardless of how the sheath 40 is applied to the gage section 20, the sheath 40 must be relatively thick. The thickness of sheath 40 can vary for different materials. While the drawings show ligament 10 as having a circular cross-section, those skilled in the art will recognize that the cross-section can be elliptical or any other shape suitable for the intended end use of the prosthesis. For example, sheath 40 may have an elliptical cross section to match the shape of a natural ligament. The ligament 10 may also be more narrow at its midportion than at its end portions.

Ligament 10 may also optionally include a core 30. The core 30 is disposed within a longitudinal bore 28 through gage section 20. The core 30 is preferably made of a biocompatible elastomer to which is added a biocompatible radiopaque material which permits radiographic visualization of the prosthetic ligament 10. The material of choice is made of between 5-25%, inclusive, barium sulfate, by weight, in a high strength block copolymer containing silicone oil. Zirconium oxide, titanium oxide or any other suitable radiopaque material may be used in place of barium sulfate. A suitable elastomer is described in Sterling U.S. Pat. No. 4,386,179, which is hereby incorporated herein by reference, and sold commercially under the trademark C-FLEX®. Sheath 40 is preferably also made of C-FLEX®.

Fixation of the ligament 10 may be provided by any suitable means, such as screws, nails or staples. The preferred means of fixation, however, is by bone screws 52, illustrated in FIG. 6. Bone screw 52 includes a large, relatively flat, rounded screw head 54 to prevent disengagement of the loop 50 and a tapered section 56 extending from the perimeter of the screw head 54 to the threaded shank. 58. The threads of shank 58 may be cancellous or cortical. The screw 52 may be self-tapping or nonself-tapping. The shank 58 might typically have a diameter of 3.5-8.0 mm (0.14-0.31 inches). The bone screw 52 which is best suited for use with the preferred embodiment of ligament 10 discussed above has a shank diameter of 5 mm (about 0.2 inch). All surfaces of the screw head 54 and tapered section 56 are smooth to minimize abrasion. The large, relatively flat screw head acts as a washer to prevent the loops 50 from disengaging.

The interaction between the loop 50 and the tapered section 56 of bone screw 52 permits tensile loading of the ligament 10 during fixation. The self-tensioning effect insures that the ligament 10 is taut when implanted and is the preferred means of providing in vivo stability of the ligament 10. The design of the screw head 54 and tapered section 56 cause the loop area to expand and the ligament 10 to undergo subsequent tensioning as the screw 52 is fully inserted. During surgery, such a tensile load is intentionally applied to secure the ligament and attain an appropriate joint response. Studies suggest that the desired tensioning ranges between about 35-90 N (8-20 lbs.) and that about 35-45 N (8-10 lbs.) is optimum. It has also been determined that the screw 52 should be inserted so that the shank 58 is aligned towards the bottom of the loop area, closest to the gage section 20 to create acceptable levels of tensile loading on the ligament 10 during fixation. The maximum prosthetic ligament loads decrease as the screw 52 is inserted more towards the bottom of the loop area.

Due to the design of the braided ligament 10, the anticipated in vivo constructional deformation (i.e., compaction of fibers and helical changes) may be minimized by the application of preloads. The applied preload should exceed the maximum physiological load which the ligament may possibly encounter in vivo. However, these preloads should be low enough so that plastic deformation of the polyethylene material is not induced and damage within loop areas is avoided.

The higher preloads would be expected to protect against additional fiber settling which may occur from occasional excessive loading. Although the polyethylene ligament has demonstrated constructional deformation less than the value of 6-8 mm (0.24-0.31 inch) characteristic of a stable knee, this settling can be reduced by preloading the ligament prior to surgery. A preload of 1000 N (225 lbs.) has been determined to be advantageous to protect the prosthetic ligament against in vivo settling resulting from occasional excessive loading.

A SPECTRA-1000 ™ polyethylene ligament, not preloaded, exhibited an average ultimate tensile strength of 9017±468 N (2026±105 lbs.) when tested at 1%/sec. with failure occurring in the loop area. Assuming a constant fiber diameter of 27 microns (0.001 inch) and calculating the number of fibers for the preferred embodiment of the prosthetic ligament (120 fibers/yarn, 6 yarns/parallel wound ply, 8 parallel wound plies/braid, and 2 braids/ligament at the loops) allows for this value of breaking strength to be converted to an ultimate stress value, 1367 MPa (198,000 psi) for the SPECTRA-1000 ™ material. The difference between the reported ultimate stress value of the SPECTRA-1000 ™ fiber, approximately 2390 MPa (425,000 psi), and the measured value for the prosthetic ligament 10 made from the SPECTRA-1000 ™ material can be attributed to loop and braid effects associated with ligament 10. Hence, the doublelooped ligament 10 has an effective ultimate tensile strength which is 47% of the strength of equivalent SPECTRA-1000 ™ fibers neglecting loop and braid effects. Thus, a preload of 1000 N (225 lbs.) is 5.2% of the breaking load (i.e., 19,108 N or 4294 lbs.) of the fiber. Commercial data (Allied-Signal Inc.) reveals that SPECTRA-1000 ™ fiber exhibits asymptotic plastic deformation behavior after approximately 24 hours for loads equivalent to 10% of the breaking load. Hence, it is apparent that negligible plastic deformation of the polyethylene material would result from an applied preload of 1000 N (225 lbs.). Short-term deformation data for ligament devices which were loaded statically under 1000 N (225 lbs.) has shown that changes in length are very low even after a few minutes, and there is negligible change in length with loading after an hour.

A statically applied preload of 1000 N (225 lbs.) for one hour appears to be optimum for the ligament made of SPECTRA ™-1000 in that constructional deformation associated with in vivo service loads is minimized and negligible permanent plastic deformation of the polyethylene material is introduced. Following preloading, the length of the prosthetic ligament increases about 2-5%, while the elongation at break (tested at 1%/sec) decreases to approximately 8% compared to 14% for a ligament in its nonpreloaded state.

Tensile tests were performed on the embodiment consisting of an 8-strand, 6-parallel wound plain braid with 5-7 picks/inch.

Double-looped SPECTRA-1000 ™ polyethylene ligaments with no core or sheath were tested to failure under tensile loading to evaluate their axial mechanical properties; breakage load, elongation to breakage and axial stiffness. Each ligament in this series of tests was approximately 17 cm in length, preloaded for one hour at 1000 N (225 lbs.) and sterilized in ethylene oxide prior to use. Strain rates of 1, 10 and 100%/per sec. were applied. The results of this series of tests are presented in Table I below.

TABLE I

| | | Tension Test Data | | |
|---|---|---|---|---|
| Strain Rate (%/sec) | Ligaments Tested | Breakage Load[1] (N) | Elongation[3] to Breakage (%) | Axial Stiffness (N/mm) |
| 1 | 6 | 9239 ± 491[2] (2076 ± 110 lbs) | 7.1 ± 0.4 | 230 ± 22 |
| 10 | 7 | 9017 ± 468 (2026 ± 105 lbs) | 6.7 ± 0.4 | 216 ± 40 |
| 100 | 6 | 8682 ± 371 (1951 ± 83 lbs) | 6.8 ± 0.6 | 266 ± 36 |

[1] The maximum force applied to the device during testing.
[2] Arithmetic mean value ± standard deviation.
[3] The change in displacement from that associated with 45 N load to that associated with the maximum load, assuming 45 N to be the approximate minimum tensile load at implant.

The axial modulus of elasticity of the SPECTRA-1000 ™ fibers is quite high and would not be expected to be flexible enough for use as a prosthetic ligament. Indeed, when tested axially in a braided configuration, the prosthetic ligament can still appear to be quite stiff following cyclic loading. However when the braided ligament is tested in the anatomical position, the modulus of elasticity is about 100,000 psi and the stiffness values come down to the range reported for the human ACL.

A series of studies were conducted under axial and anatomical conditions to observe the performance of seven braided polyethylene ligaments which were coated with a flexible, resilient polymer coating. Multiple load cycles were applied to determine the degree of change in both the stiffness and constructional deformation characteristics. Table II lists the properties of the fiber material and ultimate ligament strength for the polyethylene ligaments.

The ligaments were cyclically tensile tested on a MTS 810 servo hydraulic test system as follows:

The first 10 cycles were controlled by hand and the displacements recorded at loads of 89 N, 178 N, 267 N, 358 N and 445 N. Following the tenth cycle, the ligament was cycled at 1 Hz between 22 N and 445 N and the displacements recorded at cycles of 100, 500, and 1000. The test was terminated at the 1000th cycle. The axial test arrangement consisted of axially loading the ligament between two pin grips. For the anatomical arrangement, the ligament was secured to a prosthetic knee and loaded in an anterior drawer direction at 0, 20, and 90° of flexion.

TABLE II

Strength and Ductility Properties of the Ligaments and Coating

| | Fiber Properties (Approximate) | | |
|---|---|---|---|
| Material | Tensile Strength, MPa | % Elongation | Ligament Strength N |
| Polyethylene Ligament | 2,930 (425,000 psi) | 3 | 10,700 (2,000 lbs) |
| Coating | 14 | 700 | — |

Figure 7:
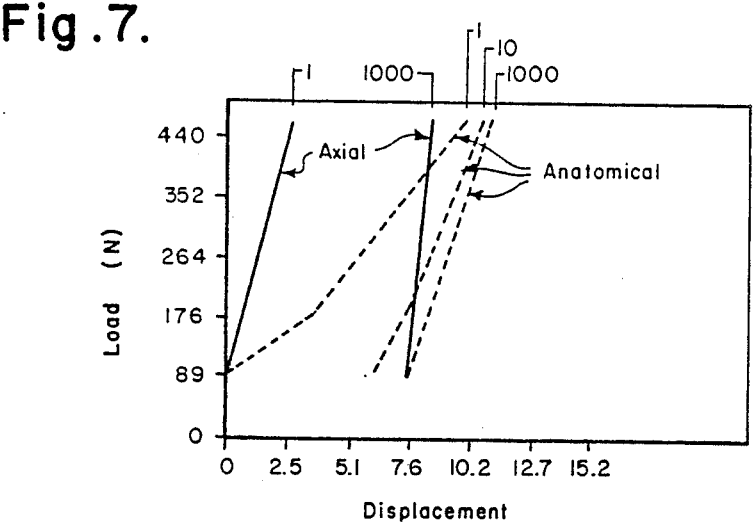
FIG. 7 is a graph showing load-deflection behavior for polyethylene prosthetic ligaments tested under axial and anatomical loading conditions.

The results of this study indicate that the degree of flexion had a minimal effect on both the stiffness and constructional deformation results. Load-deflection curves for in-vitro tests at 20° flexion are presented in FIG. 7. The curve presented is for cycles 1, 10, and 1000. Results of the non-anatomical (axial) tests are also shown for comparison. Constructional deformation was evaluated at 89 N load because prosthetic ligaments are generally inserted with a load of this magnitude using a tensioning device.

Figure 8:
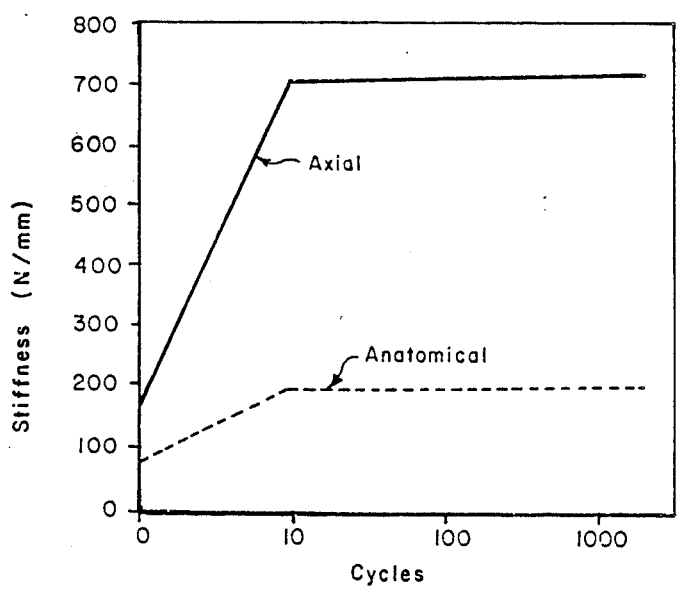
FIG. 8 is a graph showing the effect of multiple load cycles on the stiffness of polyethylene prosthetic ligaments.
Figure 9:
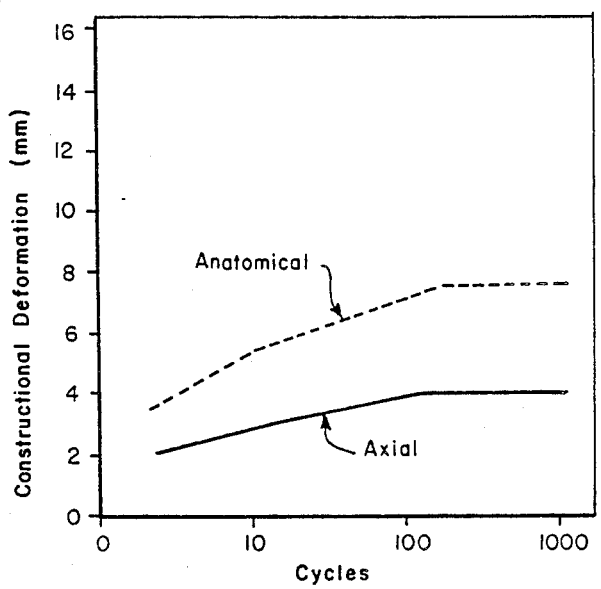
FIG. 9 is a graph showing the effect of multiple load cycles on the constructional deformation of polyethylene prosthetic ligaments.

FIGS. 8 and 9 show results of the change in stiffness and constructional deformation, respectively, as a function of load cycles.

When tested non-anatomically (axially), the polyethylene ligament showed initial (first cycle) stiffnesses of 132 N/mm. At 1000 cycles, the value increased to 700 N/mm. More importantly, the amount of constructional deformation after 1000 cycles was 12.7 mm (0.5 inch). However, under anatomical load condition, the stiffness characteristics decreased significantly while the cyclic settling increased relative to that observed in the axial tests. The stiffness of the ligaments tested anatomically was within the range of values reported for the human ACL.

The anatomical constructional deformation behavior stabilized after roughly 100 cycles for the polyethylene ligament, reaching a peak of roughly 7 mm (0.27 inch). The prosthetic ligaments evaluated in this study showed stabilization of both constructional deformation and stiffness properties after approximately 100 cycles. Importantly, the ligaments showed anatomical stiffness to be comparable to that of the human ACL.

Prosthetic ligaments like those used in the study reported immediately above, but without the polymer coating on the braid were tested in two separate studies using cadavers. The results indicate that the presence of the coating makes a negligible difference in the stiffness of the system. The results confirm that the anatomical positioning provides a ligament having a stiffness within the range of values reported for the human ACL.

A series of mechanical tests were conducted (see Table III) using a braided load bearing member made of ultra high molecular weight polyethylene. Both sheathed and unsheathed ligaments 10 were tested. These ligaments were not preloaded prior to testing.

TABLE III

| | With C-FLEX ® Sheath | Without Sheath |
|---|---|---|
| Ultimate Load | 8110 N | 10,100 N |
| Ultimate Elongation | 12.8 mm | 14.2 mm |
| Ultimate Stress* | 383 MPa | 476 MPa |
| Ultimate Strain | 6.7% | 7.5% |

TABLE III-continued

|  | With C-FLEX ® Sheath | Without Sheath |
|---|---|---|
| Energy to Failure | 89 N-m | 121 N-m |
| Stiffness (axial) | 634 N/mm | 711 N/mm |

*Nominal, using cross-sectional area at mid-section of 21.2 mm², 191 mm (7½") with 19 mm (0.75") eyelets Strain Rate = 0.9%/second Two series of axial fatigue tests were conducted on double-looped SPECTRA-1000 ™ polyethylene ligaments. Each ligament was an 8 strand, 6 parallel wound plain braid, with no sheath or core, approximately 17 cm in length, preloaded for one hour at 1000 N (225 lbs.) and sterilized in ethylene oxide prior to use. All tests were performed in 37° C. Ringer's solution on servohydraulic testing machines. In all tests, the approximate maximum strain rate with loading was 3–10%/sec.

The first series of tests included low cycle fatigue tests performed to generate data used in producing a stress-life (S-N) curve for the ligament. The results are presented in Table IV below. In each of these tests, breakage of the ligament occurred at the splice below the loop area.

TABLE IV
LOW CYCLE AXIAL FATIGUE TEST RESULTS

| MAXIMUM LOAD (N) | FREQUENCY (Hz) | CYCLES TO FAILURE |
|---|---|---|
| 4005 | 5 | 12,774,710 |
| 4895 | 4 | 372,800 |
| 4895 | 4 | 294,830 |
| 4895 | 4 | 2,768,915 |
| 5785 | 3 | 957,410 |
| 5785 | 3 | 569,030 |
| 6675 | 2 | 84,800 |
| 6675 | 2 | 40,470 |
| 7565 | 1 | 17,382 |
| 7565 | 1 | 12,973 |

Figure 10:
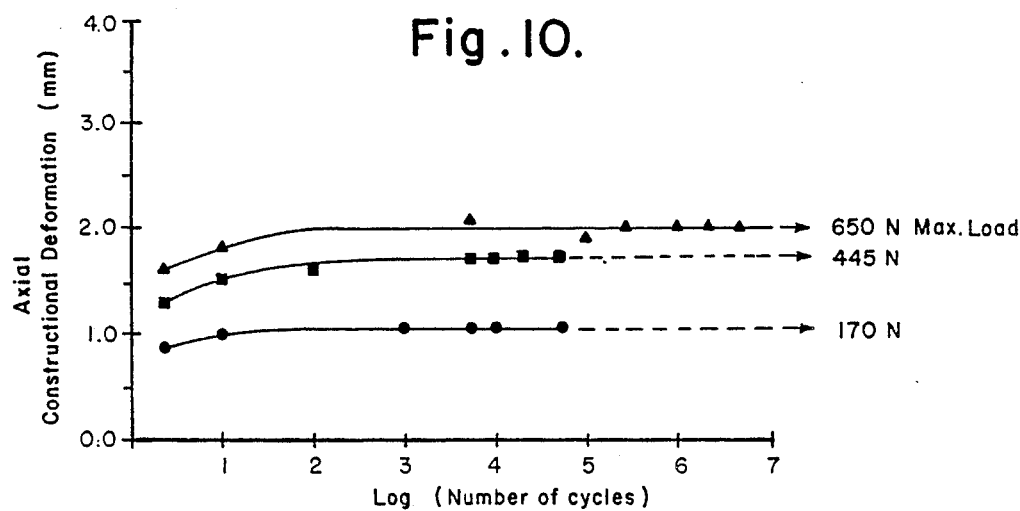
FIGS. 10 and 11 are graphs showing the axial elongation due to constructional deformation associated with various loads as a function of the number of cycles applied to the ligament.
Figure 11:
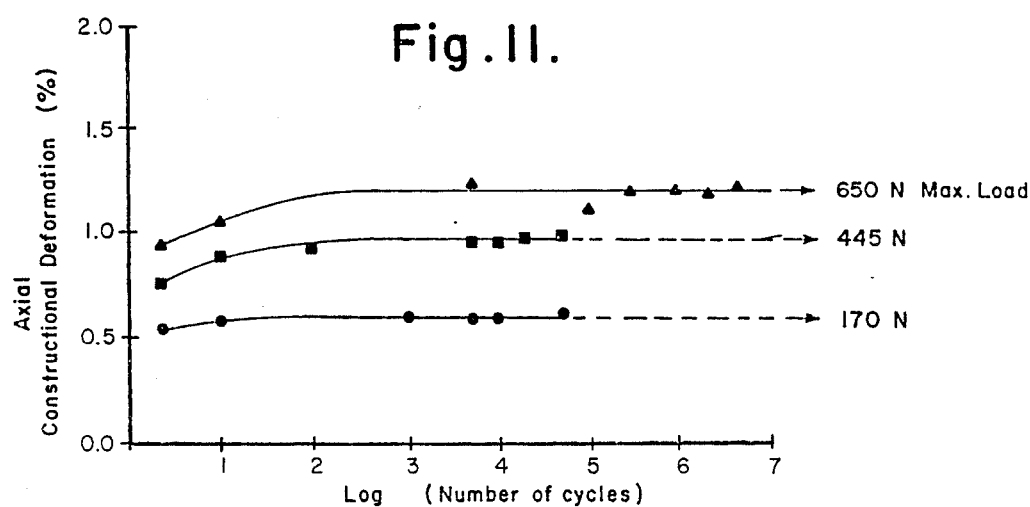

The second series of tests included tests which were conducted at levels of loading comparable to those reported for in vivo conditions including maximum applied loads of 170 N, 445 N and 650 N. From these two series of tests the axial elongation due to constructional deformation associated with each load level was evaluated as a function of the number of load cycles applied to the ligament. The results presented in FIGS. 10 and 11 indicate that, within the regime of physiological loading the elongation of the ligament due to constructional deformation becomes asymptotic after several hundred cycles and remains approximately 1.1, 1.8 and 2.1 mm (0.6, 1.0 and 1.2%) at 170 N, 445 N and 650 N, respectively. Assuming that the controlling mechanism of failure in the ligaments is rupture due to constructional deformation, the S-N data developed in the first series of tests can be used to predict a fatigue life of $8.5 \times 10^9$ cycles under a maximum cyclic load of 650 N (146 lbs.).

What is claimed is:

1. A prosthetic ligament assembly for permanently connecting first and second body members comprising:
   a prosthetic ligament having a nonaugmented load bearing member for permanently spanning the distance between said first and second body members, said load bearing member having a longitudinal gage section and two ends for attachment to said first and second body members, wherein at least one of said ends is a looped extension of said gage section continuous therewith, and said load bearing member is made from a plurality of biocompatible, high strength polyethylene yarns, each said yarn including at least fifty fibers and having a tensile strength greater than or equal to about 100,000 psi, each said fiber having an average diameter of less than about one hundred microns; and
   a bone screw for complementary engagement with said looped extension to fix said prosthetic ligament to one of said first or second body members, said bone screw having a head portion, a shank and a tapered section extending beneath said head portion to said shank for tensioning said prosthetic ligament during implantation.

2. A prosthetic ligament assembly as recited in claim 1 wherein said load bearing member is preloaded to a degree which exceeds the maximum physiological load to which said prosthetic ligament will be exposed in vivo during normal activities and which is sufficient for removing slack from said load bearing member to avoid constructional deformation of said load bearing member without inducing plastic deformation of said fibers.

3. A prosthetic ligament assembly as recited in claim 1 wherein said gage section has one said looped extension at each end thereof and there are two said bone screws.

4. A prosthetic ligament assembly as recited in claim 2 wherein said yarns are intertwined into a braid, which braid, following such preloading, has an average diameter of about four to six millimeters.

5. A prosthetic ligament assembly as recited in claim 1 further comprising a sheath encasing said gage section.

6. A prosthetic ligament assembly as recited in claim 1 wherein said gage section defines a longitudinal bore therethrough and said prosthetic ligament further comprises means disposed within said bore to permit radiographic visualization of said prosthetic ligament.

7. A prosthetic ligament assembly as recited in claim 1 wherein said load bearing member is formed from ultra high molecular weight polyethylene.

* * * * *

UNITED STATES PATENT AND TRADEMARK OFFICE
CERTIFICATE OF CORRECTION

PATENT NO. : 4,932,972

DATED : June 12, 1990

INVENTOR(S) : Richard L. Dunn and Danny H. Lewis

It is certified that error appears in the above-identified patent and that said Letters Patent is hereby corrected as shown below:

Title page , under "Other Publications, D. Butler et al.," delete "Cruciat" and substitute therefor --Cruciate--.

under "Other Publications, Prosthetic Ligament etc.," delete "Reconstruciton" and substitute therefor --Reconstruction--.

under "Other Publications, Prosthetic Ligament etc.," delete "school" and substitute therefor --School--.

under "Other Publications, C. Bolton & W. Bruchman etc., delete "as" and substitute therefor --at--.

Col. 2, line 20, underline the word "supra".

Col. 2, line 25, underline the word "supra".

Col. 4, line 34, underline the words "in vivo".

Col. 6, line 64, delete "ga-ge" and substitute therefor --gage--.

Col. 7, line 53, delete "shank." first instance, and substitute --shank-- therefor.

Col. 7, line 68, underline the words "in vivo".

Col. 8, line 17, underline the words "in vivo".

Col. 8, line 21, underline the words "in vivo".

Col. 8, line 35, underline the words "in vivo".

UNITED STATES PATENT AND TRADEMARK OFFICE
CERTIFICATE OF CORRECTION

PATENT NO. : 4,932,972                          Page 2 of 3

DATED : June 12, 1990

INVENTOR(S) : Richard L. Dunn and Danny H. Lewis

It is certified that error appears in the above-identified patent and that said Letters Patent is hereby corrected as shown below:

Col. 8, line 44, delete " - " after the word "plies/".

Col. 8, line 62, delete "lbads" and substitute therefor --loads--.

Col. 9, line 5, delete "SPECTRA TM-1000" and substitute therefor --SPECTRA-1000TM--.

Col. 9, line 6, underline the words "in vivo".

Col. 9, line 23, delete "per" after 100% /.

UNITED STATES PATENT AND TRADEMARK OFFICE
CERTIFICATE OF CORRECTION

PATENT NO. : 4,932,972

DATED : June 12, 1990

INVENTOR(S) : Richard L. Dunn and Danny H. Lewis

It is certified that error appears in the above-identified patent and that said Letters Patent is hereby corrected as shown below:

Title page   under "Other Publications, C. Peterson et al.," delete "segmented" and substitute therefor --Segmented--.

Signed and Sealed this

First Day of September, 1992

Attest:

DOUGLAS B. COMER

Attesting Officer

Acting Commissioner of Patents and Trademarks